(12) United States Patent
Fladoos

(10) Patent No.: US 12,115,098 B1
(45) Date of Patent: Oct. 15, 2024

(54) PHYSIO TAPE WITH INDUCTIVE HEATING SYSTEM

(71) Applicant: Jason Fladoos, Santa Monica, CA (US)

(72) Inventor: Jason Fladoos, Santa Monica, CA (US)

( * ) Notice: Subject to any disclaimer, the term of this patent is extended or adjusted under 35 U.S.C. 154(b) by 0 days.

(21) Appl. No.: 18/215,749

(22) Filed: Jun. 28, 2023

Related U.S. Application Data

(63) Continuation-in-part of application No. 15/931,753, filed on May 14, 2020, now Pat. No. 11,723,810.

(51) Int. Cl.
*A61F 7/00* (2006.01)
*A61F 13/04* (2006.01)
(Continued)

(52) U.S. Cl.
CPC .............. *A61F 7/007* (2013.01); *A61F 13/04* (2013.01); *H05B 6/06* (2013.01); *H05B 6/105* (2013.01); *A61F 2007/009* (2013.01); *A61F 2007/0093* (2013.01); *A61F 2007/0094* (2013.01); *A61F 2007/0096* (2013.01)

(58) Field of Classification Search
CPC .......... A61F 13/0273; A61F 7/03; A61F 7/10; A61F 7/0241; A61F 7/007; A61F 2007/0225; A61F 2007/0226; A61F 2007/0078; A61F 2007/0071; A61F 13/0283; A61F 13/046; A61F 5/0104; A61F 2013/00655; A61F 2013/00489; A61F 13/023; A61F 7/106; A61F 2007/0219; A61F 2013/00187; A61F 13/00051; H05B 3/0023; H05B 3/06; H05B 3/34; H05B 2203/036; A61L 15/14; A61L 15/12

See application file for complete search history.

(56) References Cited

U.S. PATENT DOCUMENTS

| 9,735,893 B1 * | 8/2017 | Aleksov | A61B 5/0024 |
| 2005/0007406 A1 * | 1/2005 | Haas | H05B 3/84 |
| | | | 347/17 |

(Continued)

FOREIGN PATENT DOCUMENTS

| CN | 104887384 A * | 9/2015 | A61B 5/01 |
| CN | 106237519 A * | 12/2016 | |

(Continued)

*Primary Examiner* — Tarla R Patel
(74) *Attorney, Agent, or Firm* — William J. Benman; Benman, Brown & Williams

(57) ABSTRACT

An inductive heating system including a tape with a mechanism for securing a physio tape to the body of a user. An inductive heating element is mounted on or in the tape and is adapted to receive magnetic energy from a remote inductive heating source. In one embodiment, the system further includes a control system operationally coupled to the heating source. A user interface is coupled to the control system to set a temperature profile of the system as a function of time. A first transceiver is coupled to the control system to communicate the program to a second transceiver remotely mounted at the tape. The second transceiver mounted on the tape receives information from a temperature sensor mounted on the tape and sends on and off signals to back to the control system to regulate the flow of energy to the tape and thereby execute the temperature regulation program. The inductive heating source may be mounted in a stationary frame or a mobile wireless platform.

14 Claims, 6 Drawing Sheets

(51) Int. Cl.
  *H05B 6/06* (2006.01)
  *H05B 6/10* (2006.01)

(56) References Cited

U.S. PATENT DOCUMENTS

| | | | | |
|---|---|---|---|---|
| 2006/0060576 A1* | 3/2006 | Haas | | A61F 7/007 |
| | | | | 219/543 |
| 2008/0195018 A1* | 8/2008 | Larson | | A61F 13/085 |
| | | | | 602/53 |
| 2013/0061370 A1* | 3/2013 | Ezell | | A61F 7/02 |
| | | | | 607/109 |
| 2014/0074006 A1* | 3/2014 | Manley, Jr. | | A61F 13/122 |
| | | | | 602/74 |
| 2014/0352325 A1* | 12/2014 | Brown | | F25B 21/04 |
| | | | | 62/3.2 |
| 2016/0262924 A1* | 9/2016 | Abreu | | A43B 7/005 |
| 2019/0374362 A1* | 12/2019 | Anderson | | A61F 7/10 |
| 2020/0121497 A1* | 4/2020 | Shr | | A61F 13/0233 |
| 2020/0238098 A1* | 7/2020 | Chornenky | | A61N 2/002 |
| 2020/0352781 A1* | 11/2020 | Yang | | A61F 7/007 |
| 2021/0177432 A1* | 6/2021 | Rapp | | A61B 17/1355 |
| 2021/0369498 A1* | 12/2021 | Costello | | A61F 7/02 |
| 2022/0160540 A1* | 5/2022 | Wang | | A61F 7/08 |

FOREIGN PATENT DOCUMENTS

| | | | | |
|---|---|---|---|---|
| CN | 107361904 A | * | 11/2017 | |
| CN | 108784921 A | * | 11/2018 | |
| CN | 109124864 A | * | 1/2019 | A61F 7/02 |
| CN | 110200739 A | * | 9/2019 | |
| CN | 209713997 U | * | 12/2019 | |
| KR | 915320 B1 | * | 9/2009 | A61F 7/007 |
| KR | 200490097 Y1 | * | 7/2018 | |
| WO | WO-2010140818 A2 | * | 12/2010 | A61N 1/22 |
| WO | WO-2021077152 A1 | * | 4/2021 | A41D 13/0015 |

* cited by examiner

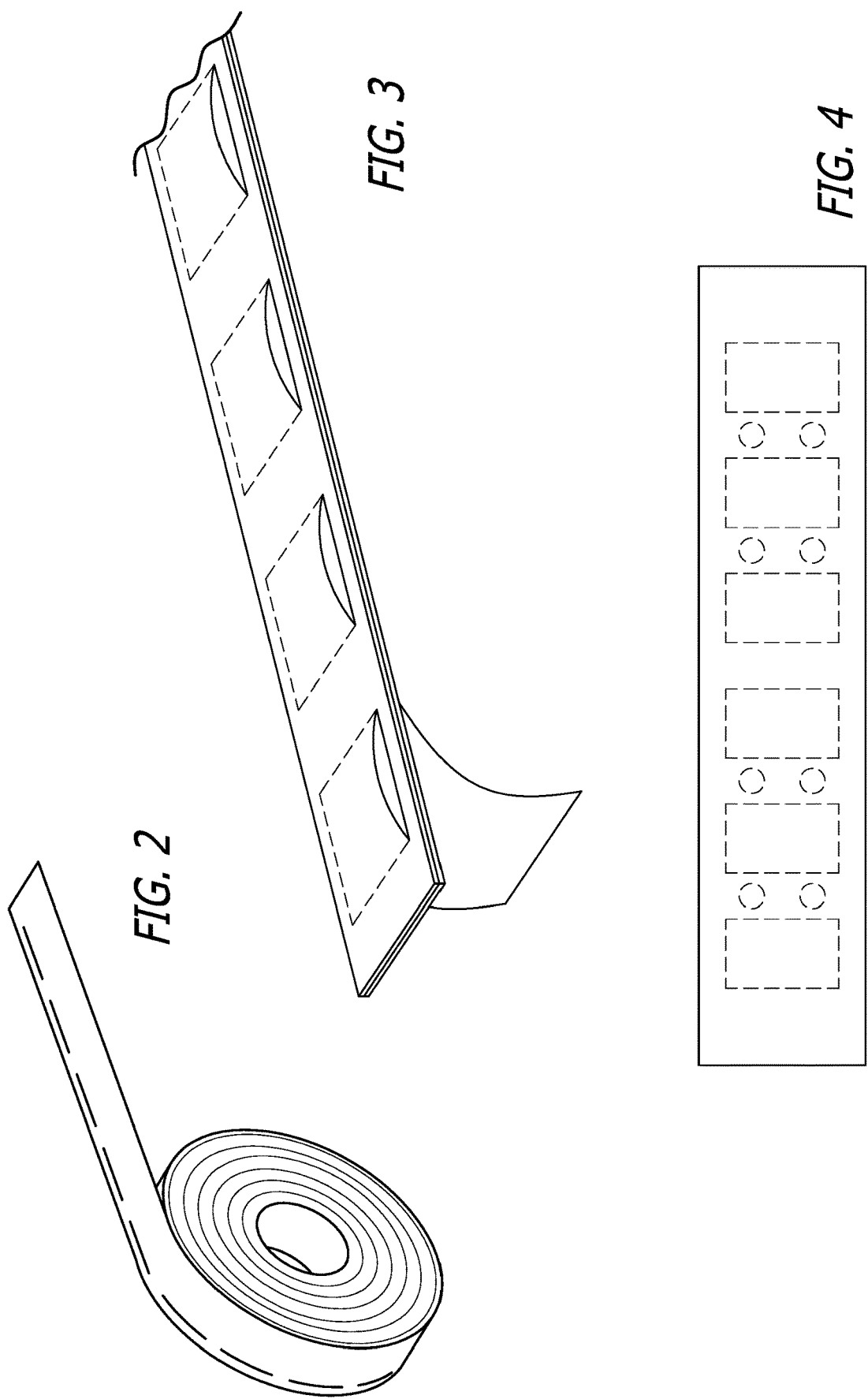

PHYSIO TAPE WITH INDUCTIVE HEATING SYSTEM

BACKGROUND OF THE INVENTION

Field of the Invention

The present invention relates to tapes and bindings. More specifically, the present invention relates to therapeutic physio and kinesiology tapes and bindings with thermal properties.

Description of the Related Art

Physio tape (aka kinesiology tape) is a tape that is used for treating athletic injuries and a variety of physical disorders. Physio tape is conventionally a thin, stretchy, elastic cotton strip with an acrylic adhesive. Therapeutic physio tape can be used to treat inflammation as well as a wide variety of musculoskeletal and sports injuries. Physio tape may be manufactured to emulate human skin in both thickness and elasticity to allow the tape to be worn without binding, constriction or restriction of movement.

Physio tapes generally provide support. However, therapists are likely to appreciate that there is a need in the art for a tape that provides support as well as thermal properties such as heat or cold.

The need in the art was addressed by U.S. Pat. No. 10,492,957 entitled Flexible Adhesive Physio Tape with Thermal Properties, issued Dec. 3, 2019 to J. Fladoos (hereinafter 'Fladoos-1'); U.S. Pat. No. 10,350,109 entitled Flexible Adhesive Physio Tape with Cooling Properties, issued Jul. 16, 2019 to J. Fladoos (hereinafter 'Fladoos-2'); U.S. Pat. No. 10,342,889 entitled Electrically Actuated Adhesive Physio Tape with Thermal Properties, issued Jul. 9, 2019 to J. Fladoos (hereinafter 'Fladoos-3') and U.S. patent application Ser. No. 15/931,753 entitled Modular Physio Tape With Thermal Properties, issued Aug. 15, 2023 to J. Fladoos (hereinafter 'Fladoos-6' or 'the Parent Application') as U.S. Pat. No. 11,723,810 the teachings of all of which are hereby incorporated by reference herein.

These patents disclose and claim various physio tape designs with thermal heating and cooling properties. While these designs substantially addressed the need in the art, a further need remains for a design capable of inductive heating as an inductive heating system would enable the tape to be more effective in heating over a longer period of time and be potentially less expensive to manufacture relative to other heating systems.

SUMMARY OF THE INVENTION

The need in the art is addressed by the tape with an inductive heating system of the present invention. In the illustrative embodiment, the tape has a mechanism for securing a material to the body of a user. An inductive heating element is mounted on or in the material and is adapted to receive magnetic energy from a remote inductive heating source.

In the best mode, the system further includes a control system operationally coupled to the heating source. A user interface is coupled to the control system to set a temperature profile of the system as a function of time. A first transceiver is coupled to the control system to communicate the program to a second transceiver remotely mounted at the tape. The second transceiver receives information from a temperature sensor mounted on the tape and sends on and off signals to back to the control system to regulate the flow of energy to the tape and thereby execute the temperature regulation program. The inductive heating source may be mounted in a stationary frame or a wireless mobile platform such as a wand.

In a preferred embodiment, the invention further includes an analog or digital system for pairing the inductive heater to the inductive heating source and automatically deactivating the inductive heating source upon receipt of a signal from an inductive element to which the inductive heating system is paired or not to be paired.

BRIEF DESCRIPTION OF THE DRAWINGS

FIG. 2 is a diagram showing a roll of the illustrative embodiment of the tape of the present invention.

FIG. 3 is a perspective view showing a segment of the tape of FIG. 2 with pockets partially in phantom and a backing sheet partially removed.

FIG. 4 is the top view of the tape shown in FIG. 3 with heating elements and electronics thereof shown in phantom.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
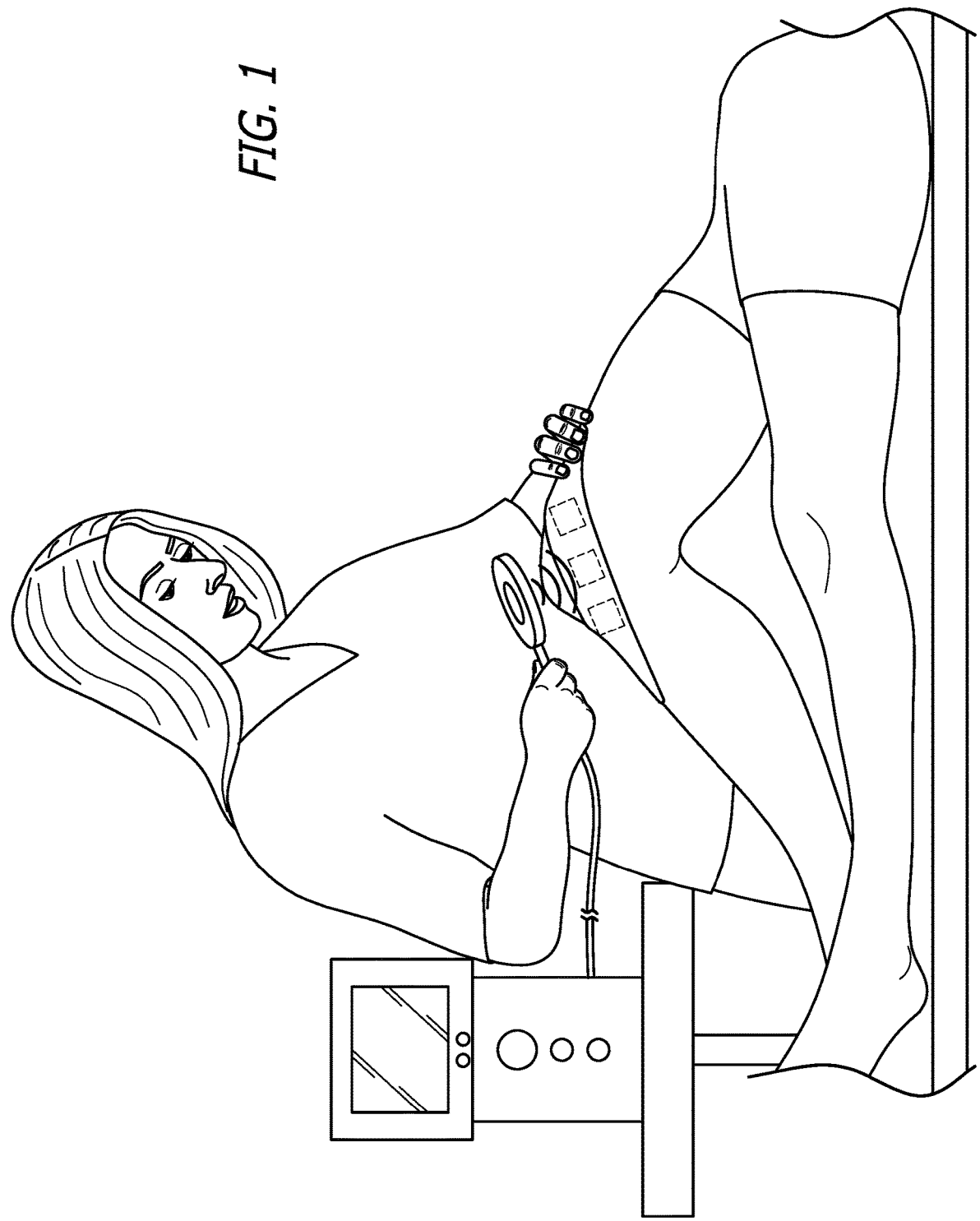
FIG. 1 is a diagram showing the tape with an inductive heating system of the present invention in operation.

FIG. 1 is a diagram showing the tape with an inductive heating system of the present invention in operation. As illustrated in FIG. 1, a key feature of the invention is the mounting of an inductive heating element, shown in phantom, on or in a tape or pad of material, designed to receive magnetic energy from a remote inductive heating source shown as an inductive heater. In the embodiment of FIG. 1, the inductive heater is powered by a power supply in response to inputs provided by an operator via a user interface.

In the embodiment of FIG. 1, the inductive heater is coupled to the power supply by a cord and used to treat a patient by a therapist. In alternative embodiments disclosed below, the inductive system of the present invention is implemented without the requirement of a therapist.

FIG. 2 is a diagram showing a roll of the illustrative embodiment of the tape of the present invention. The tape of the present invention is optionally implemented, in the illustrative embodiment, with a segment of material, such as off the shelf physio tape, or flexible, elastic pad, with an adhesive on one side thereof, or another mechanism, hereinafter 'the tape', for securing the material to the body of a user. In any case, In FIG. 2, the tape is shown in a roll with slit openings to receive inductive heating elements as discussed more fully below. In the illustrative embodiment, the tape or pad, of the present invention, hereinafter the 'tape', is optionally implemented with a material, such as conventional physio tape, or a flexible elastic pad, with an adhesive on one side thereof, or another mechanism, for securing the material to the body of a user. In any case, the tape is filled with heating elements comprising a conductive material adapted to respond to a changing magnetic field, from the external inductive heating source described above, by yielding heat energy.

FIG. 3 is a perspective view showing a segment of the tape of FIG. 2 with pockets partially in phantom and a backing sheet partially removed. In the embodiment of FIG. 3, the heating elements are added to the tape via plural open-ended pockets. In the best mode, the pockets are implemented in the manner disclosed and claimed in patent application Ser. No. 15/931,753, entitled MODULAR PHYSIO TAPE WITH THERMAL PROPERTIES now issued as U.S. Pat. No. 11,723,810, the teachings of which are hereby incorporated by reference herein. However, the present invention is not limited to the manner by which the heating elements are secured to the tape or pad. That is, the heating elements can be sewn into the tape and added in any orientation deemed suitable for a selected application.

FIG. 4 is the top view of the tape shown in FIG. 3 with heating elements and electronics thereof shown in phantom. Also shown in phantom are optional electronic elements such as transceivers, thermostats, etc. as discussed more fully below.

Figure 5:
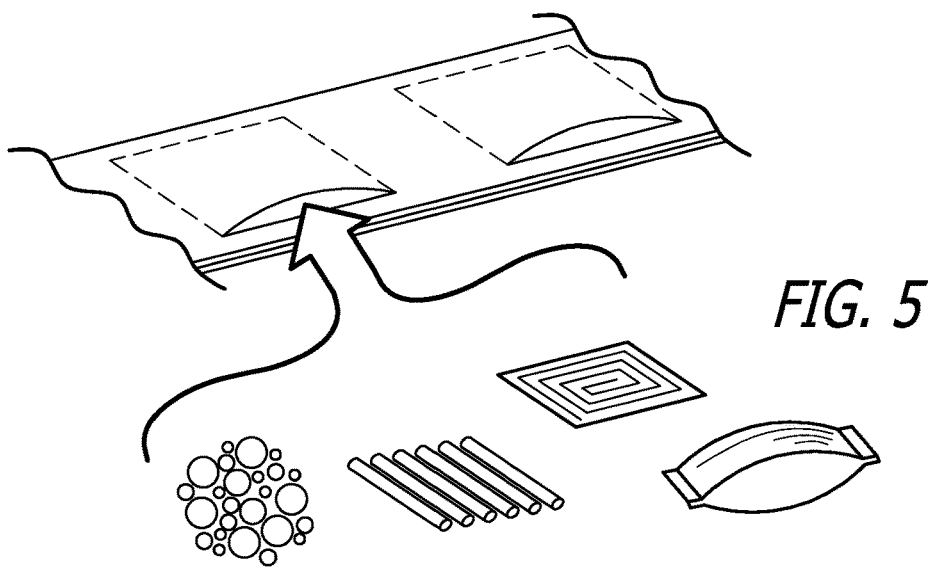
FIG. 5 is a perspective view of a segment of the tape shown in FIG. 3 with examples of inductive material adapted to be retained in the pockets thereof.

FIG. 5 is a perspective view of a segment of the tape shown in FIG. 3 with examples of inductive material adapted to be retained in the pockets thereof. FIG. 5 illustrates examples of inductive elements and material, such as metal beads, wire, coils etc., that can be inserted into the pockets of the tape in accordance with the present teachings.

Figure 6:
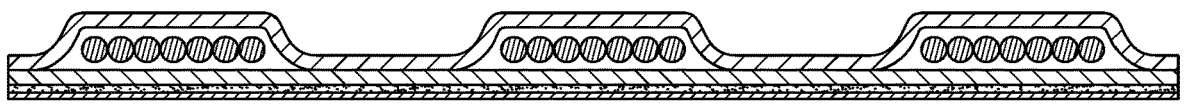
FIG. 6 is a side elevational view of the tape shown in FIGS. 3 and 5 partially in section to illustrate the multilayer structure thereof along with the inductive material therein.

FIG. 6 is a side elevational sectional view of the tape shown in FIGS. 3 and 5 that shows the multilayer structure thereof along with the inductive material inserted in the pockets thereof.

Figure 7:
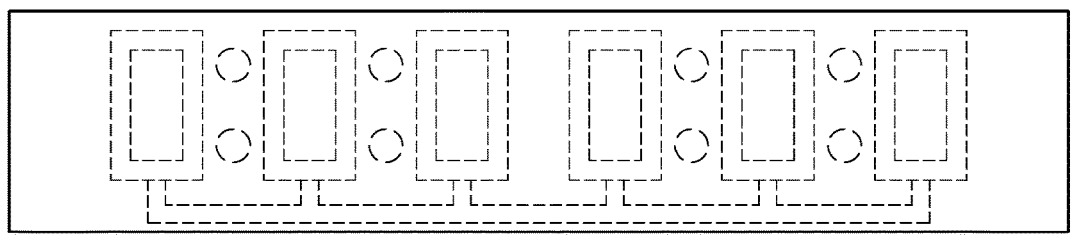
FIG. 7 is an alternative embodiment of the top view of the tape shown in FIG. 3 with heating elements and electronics thereof shown in phantom as being coupled via a ribbon cable.

FIG. 7 is an alternative embodiment of the top view of the tape shown in FIG. 3 with heating elements and electronics thereof shown in phantom as being coupled via a ribbon cable.

In the best mode, the system shown in FIG. 1 includes a control system operationally coupled to the heating source. The control system is illustrated in FIG. 8 below.

Figure 8:
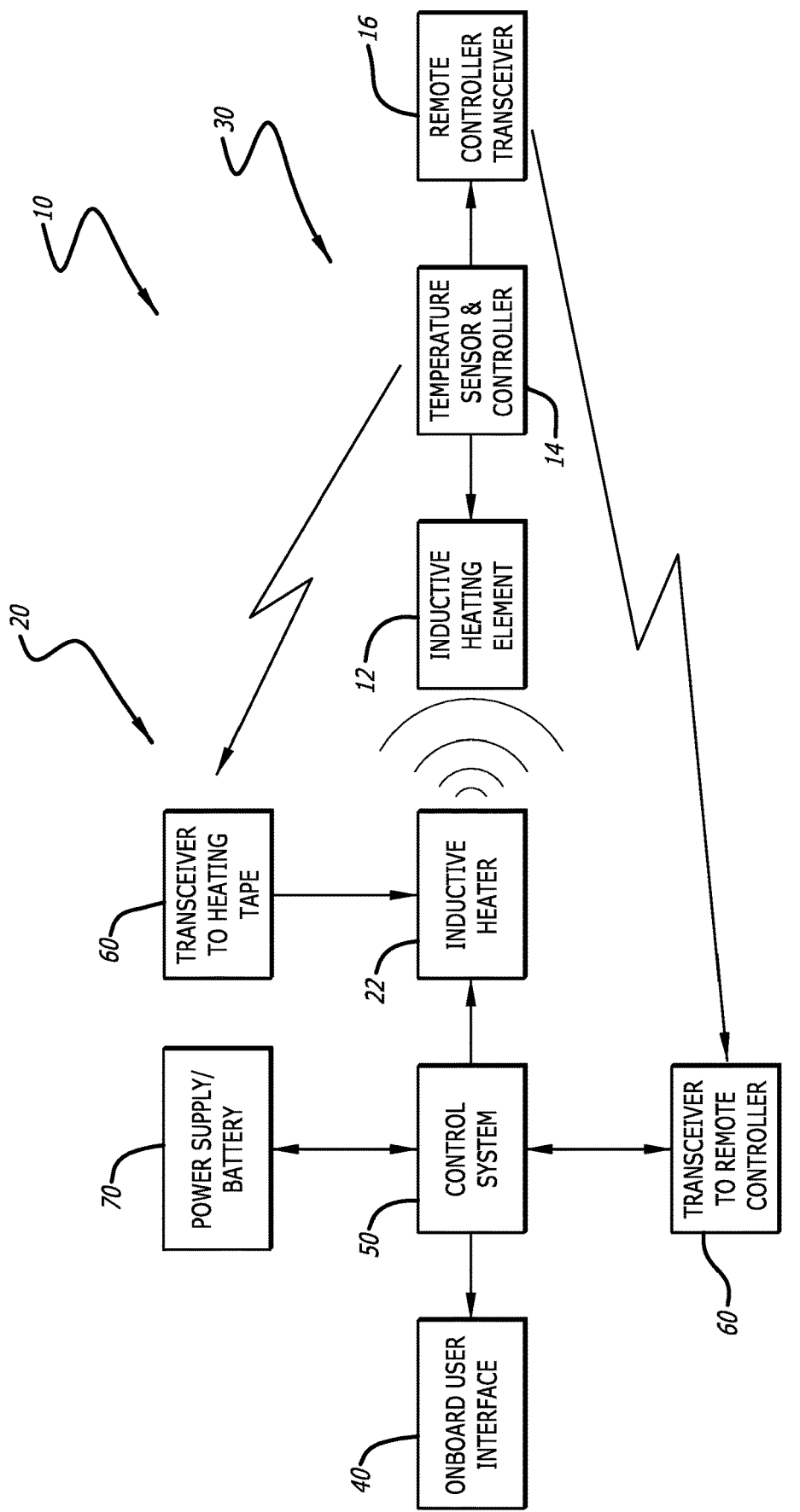
FIG. 8 is a high level block diagram of an illustrative embodiment of the heating system of FIG. 1 including the inductive heating element, inductive heater and respective control and communication subsystems.

FIG. 8 is a high level block diagram of an illustrative embodiment of the heating system 10 of FIG. 1 including the inductive heating element 12, inductive heater 22 and respective control and communication subsystems. The control system 50 may be implemented with a processor (not shown) adapted to execute software stored on a tangible medium (not shown). As an alternative, the control system could be implemented with a simple electronic circuit. Those of ordinary skill in the art will appreciate that the control system may be implemented with many schemes depending on the requirements of the application.

As shown in FIG. 8, a user interface 40 is coupled to the control system 50 to set a desired operational paradigm of the system 10 such as a level of magnetic induction and/or temperature profile as a function of time.

A first transceiver 60 is coupled to the control system 50 to communicate the program to a second transceiver 16 remotely mounted at the tape 30. The second transceiver 16 receives information from a temperature sensor 14 mounted on the tape 30 and sends on and off signals to back to the control system 50, via the first or an optional second transceiver 60, to regulate the flow of energy to the tape 30 and thereby execute a selected temperature regulation program.

In operation, the control system 50 selectively activates the inductive heater 22 with energy from the power supply 70. The power supply can be a source of line current or a simple battery. The output of the power supply 70 can be an alternating current or a direct current, depending on the design of the inductive heater or the inductive heating element. Inductive heaters 22 are well known in the art. See for example the simple inductive heating circuit illustrated in FIG. 9 below.

Figure 9:
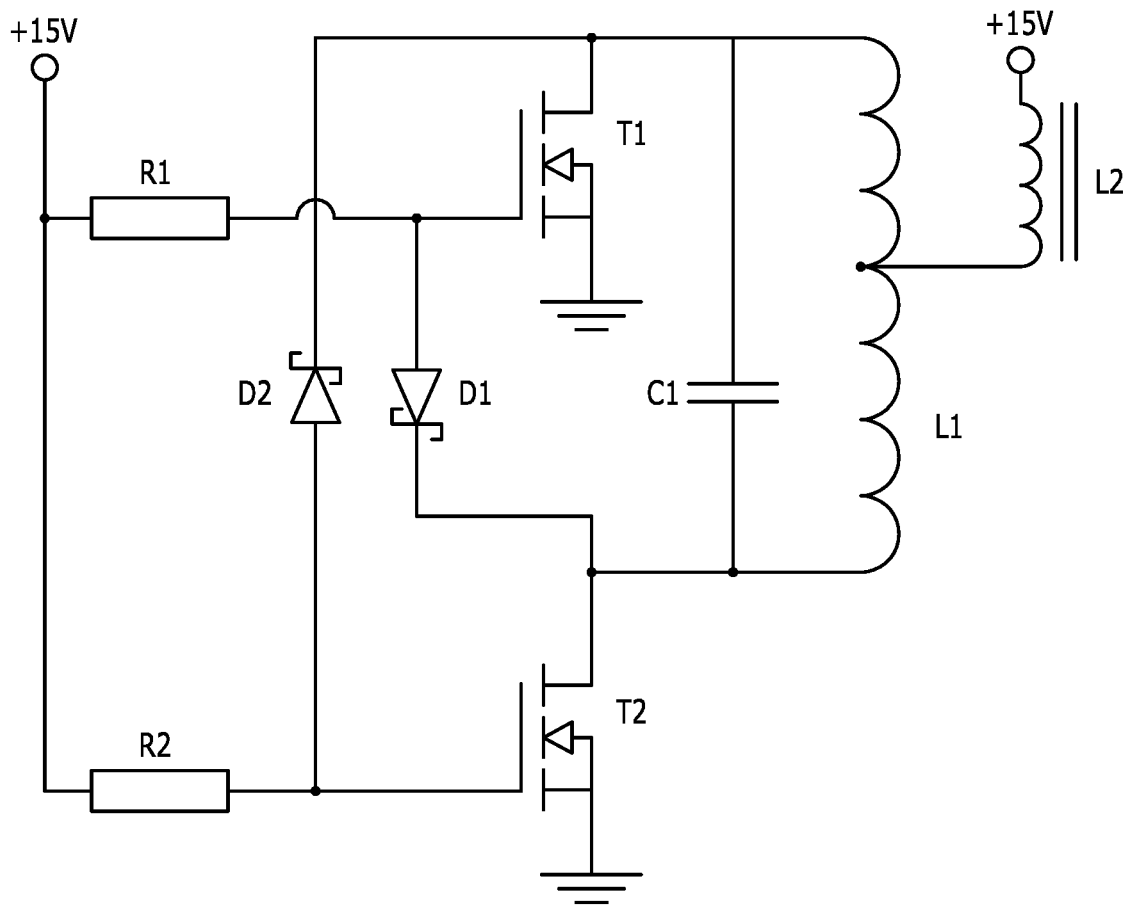
FIG. 9 is a schematic diagram of an illustrative embodiment of a simple conventional induction heating system as published by RM Cerbernetics.

FIG. 9 is a schematic diagram of an illustrative embodiment of a simple induction heating system as published by RM Cerbernetics. Those of ordinary skill in the art will appreciate that the electronic circuit should be designed to suite the requirements of the application. The key is to induce a changing magnetic field into conductive material in the tape effective to cause the temperature of the tape to increase and thereby provide a therapeutic benefit to a user.

In a preferred embodiment, for safety purposes, the system 10 may further include an analog or digital system for pairing the inductive heater to the inductive heating source and/or a system for automatically deactivating the inductive heating source upon receipt of a signal from an inductive element to which the inductive heating system is to be inductively coupled or paired or not to be paired. For example, the system may be programmed to operate only in the presence of the magnetic field of a single heating element or group of heating elements in a single tape. Further, the system can be programmed to deactivate the heating source upon detection of an unpaired inductive element. On the other hand, the system can be programmed to deactivate upon detection of a pacemaker or other sensitive device within range of the magnetic flux produced by the inductive heating element. For this purpose, pairing is useful but not required. However, pairing would allow for select heating elements to be activated or deactivated depending on the therapeutic protocol selected for a given patient.

The inductive heating source 22 may be mounted in a stationary frame or a mobile platform such as a wand. These embodiments are illustrated in FIGS. 10-12.

Figure 10:
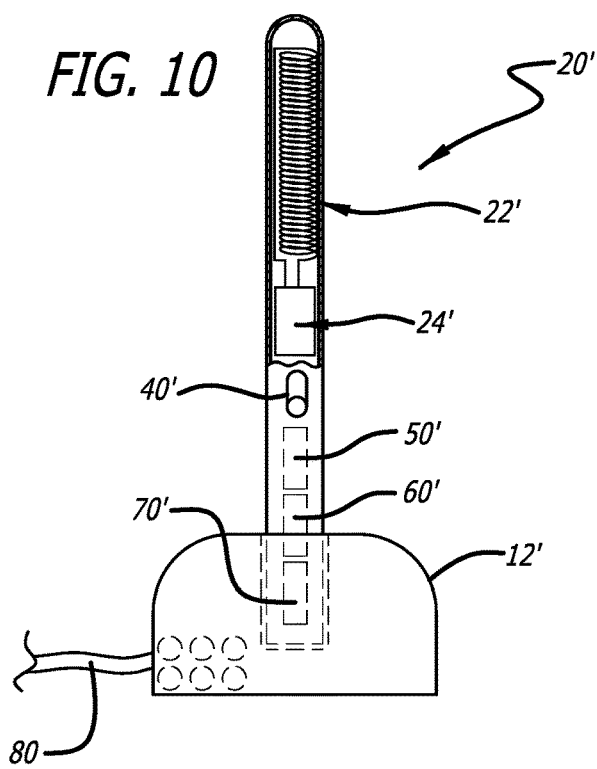
FIG. 10 is a diagram of a side view of an alternative wireless battery powered wand embodiment of the inductive heater of the present invention, partially in section, in a charging stand.

FIG. 10 is a diagram of a side view of an alternative wireless battery powered wand embodiment of the inductive heater of the present invention, partially in section, in a charging stand.

Figure 11:
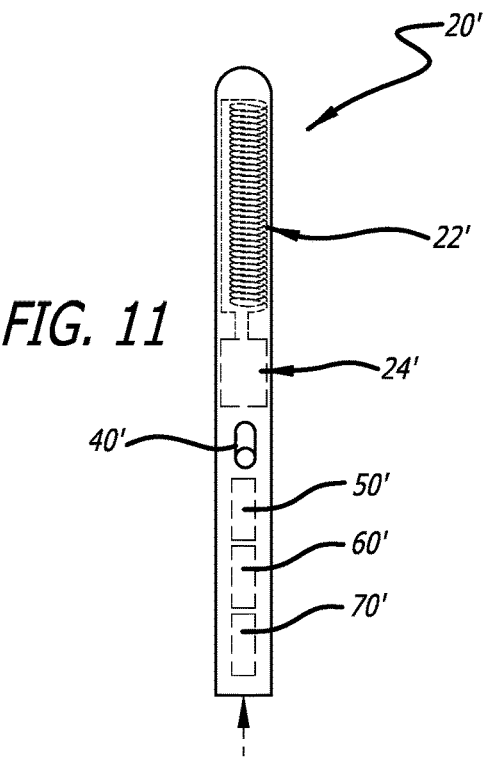
FIG. 11 is a diagram of the alternative battery powered wand embodiment of the inductive heating element shown in FIG. 10 with the wand elevated above the charging stand.
Figure 12:
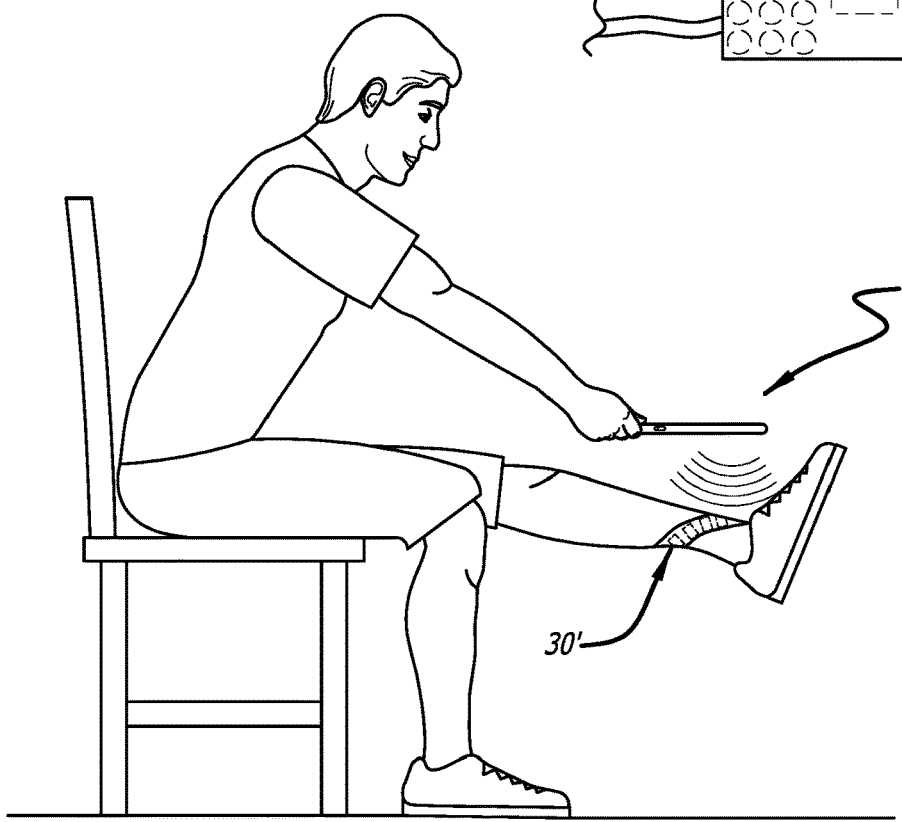
FIG. 12 is a diagram showing the wand depicted in FIGS. 10 and 11 in an illustrative application by a user.

FIG. 11 is a diagram of the wireless battery powered wand 20' shown in FIG. 10 with the wand out of the charging stand.

As shown in FIGS. 10 and 11, the wand 20' includes a coil 22' that provides a magnetic flux and thereby serves as the inductive heater depicted in FIG. 8. The coil 22' is powered by an optional DC/AC converter 24' under the control of a controller 50'. The controller 50' is coupled to a transceiver 60' and a rechargeable battery 70'. The wand 20' operates in response to activation of a switch 40'. In this embodiment, the heating program is input via a user interface (not shown) integrated into the charging stand 12. The program is transmitted to the wand 20' either directly during charging or via the transceiver 60' onboard the wand 20' by way of a transceiver (not shown) in the charging stand 12'.

FIG. 12 is a diagram showing the wand depicted in FIGS. 10 and 11 in an illustrative application by a user. In this application, a magnetic flux is provided to an inductive heating element (not shown) in a tape assembly 30' wrapped around the ankle of a user.

Those of ordinary skill in the art will appreciate that the present teachings are not limited to the illustrative embodiments provided herein. For example, the present teachings may be implemented in a chair, bed, sofa or any other piece of furniture suitable for a given application.

It is therefore intended by the appended claims to cover any and all such applications, modifications and embodiments within the scope of the present invention.

The invention claimed is:

1. A physio tape with an inductive heating system for therapeutic benefit comprising:
    a tape or pad of material having a surface with a mechanism for securing the material to a user;
    an inductive heating element mounted on or in said tape or pad of material; and
    an inductive heating source magnetically coupled to the inductive heating element.

2. The invention of claim 1 further including a control system operationally coupled to the heating source.

3. The invention of claim 2 further including a user interface coupled to the control system.

4. The invention of claim 2 further including a first transceiver coupled to the control system.

5. The invention of claim 4 further including a second transceiver coupled to the inductive heating source.

6. The invention of claim 1 further including a control system operationally coupled to the heating element.

7. The invention of claim 1 wherein the tape includes a temperature sensor for sensing a temperature of the heating element.

8. The invention of claim 7 further including a remote controller and transceiver coupled to the temperature sensor.

9. The invention of claim 1 wherein the inductive heating source is mounted in a stationary housing.

10. The invention of claim 1 wherein the inductive heating source is mounted in a wireless housing.

11. The invention of claim 1 further including means for effecting a deactivation of the heating source upon detection of an unpaired inductive element.

12. A method for providing heat to a physio tape comprising the steps of:
    providing a tape or pad of material having a surface with a first mechanism for securing the material to a body of a user;
    providing an inductive heating element on or in said tape or pad of material; and
    energizing an inductive heating source to provide a magnetic field operationally coupled to the inductive heating element.

13. The invention of claim 12 further including the step of controlling the magnetic transfer of energy from the heating source to the inductive heating element.

14. The invention of claim 13 wherein the step of controlling the transfer of energy is effectuated via a control system.

* * * * *